United States Patent
Ernst et al.

(10) Patent No.: US 12,138,583 B2
(45) Date of Patent: Nov. 12, 2024

(54) PROCESS FOR REMOVAL OF ACID GASES FROM A FLUID STREAM WITH A LIQUID ABSORBENT COMPRISING A PIPERAZINE RING

(71) Applicant: BASF SE, Ludwigshafen am Rhein (DE)

(72) Inventors: Martin Ernst, Ludwigshafen am Rhein (DE); Thomas Ingram, Ludwigshafen am Rhein (DE); Gerald Vorberg, Ludwigshafen am Rhein (DE); Georg Sieder, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 717 days.

(21) Appl. No.: 17/431,872

(22) PCT Filed: Feb. 14, 2020

(86) PCT No.: PCT/EP2020/053924
§ 371 (c)(1),
(2) Date: Aug. 18, 2021

(87) PCT Pub. No.: WO2020/169477
PCT Pub. Date: Aug. 27, 2020

(65) Prior Publication Data
US 2022/0152551 A1 May 19, 2022

(30) Foreign Application Priority Data
Feb. 18, 2019 (EP) ..................................... 19157704

(51) Int. Cl.
*B01D 53/14* (2006.01)
*C07D 295/13* (2006.01)
*C10L 3/10* (2006.01)

(52) U.S. Cl.
CPC ..... *B01D 53/1493* (2013.01); *B01D 53/1425* (2013.01); *B01D 53/1468* (2013.01);
(Continued)

(58) Field of Classification Search
CPC ............ B01D 53/1493; B01D 53/1425; B01D 53/1468; B01D 2252/20447;
(Continued)

(56) References Cited

U.S. PATENT DOCUMENTS 3,865,791 A * 2/1975 Brinkmann ........ C08G 18/3296
528/80
4,110,328 A * 8/1978 Diamond .............. C07C 335/38
536/18.2
(Continued)

FOREIGN PATENT DOCUMENTS

DE 4027249 A1 3/1992
EP 0121109 A2 10/1984
(Continued)

OTHER PUBLICATIONS

International Preliminary Report on Patentability (Chapter II) received for PCT Patent Application No. PCT/EP2020/053924, mailed on May 31, 2021, 10 pages.
(Continued)

*Primary Examiner* — Dung H Bui
(74) *Attorney, Agent, or Firm* — Faegre Drinker Biddle & Reath LLP

(57) ABSTRACT

A process for removal of acid gases from fluid stream, wherein the fluid stream is brought into contact with an absorbent to obtain a treated fluid stream and a laden absorbent, the absorbent comprising a diluent and a compound of the general formula (I) wherein $R^1$ is selected from $C_1$-$C_8$-alkyl and $C_2$-$C_8$-hydroxyalkyl; $R^2$ is selected from hydrogen and $C_1$-$C_8$-alkyl; $R^3$ is selected from hydrogen and $C_1$-$C_8$-alkyl; $R^4$ is selected from hydrogen and $C_1$-$C_8$-alkyl; $R^5$ is $C_1$-$C_8$-alkyl; with the proviso that at least one of the following conditions (i) and (ii) is met: (i) $R^5$ is $C_3$-$C_8$-alkyl bound to the nitrogen atom via a secondary or tertiary carbon atom; (ii) when $R^4$ is hydrogen, $R^3$ is $C_1$-$C_8$-alkyl; or when $R^4$ is $C_1$-$C_8$-alkyl, at least one of $R^2$ and $R^3$ is $C_1$-$C_8$-alkyl; and n is an integer from 0 to 6. Further provided is an absorbent for the absorption of acid gases from a fluid stream, comprising a diluent and a compound of the general formula (I) as defined above, as well as the use of a compound of the general formula (I) as defined above for removal of acid gases from a fluid stream. The absorbents are useful for the selective removal of hydrogen sulfide from fluid streams and have high acid gas loading capacity, high stability, and low volatility.

(Continued)

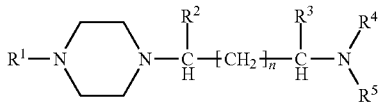

(I)

9 Claims, 3 Drawing Sheets

(52) U.S. Cl.
CPC ............ *C07D 295/13* (2013.01); *C10L 3/103* (2013.01); *C10L 3/104* (2013.01); *B01D 2252/20447* (2013.01); *C10L 2290/541* (2013.01)

(58) Field of Classification Search
CPC .... B01D 2252/20478; B01D 2252/504; B01D 2257/504; B01D 2258/0283; B01D 2258/05; C07D 295/13; C10L 3/103; C10L 3/104; C10L 2290/541; C10L 3/102; Y02C 20/40
See application file for complete search history.

(56) References Cited

U.S. PATENT DOCUMENTS

| | | | | |
|---|---|---|---|---|
| 4,405,578 | A * | 9/1983 | Sartori | B01D 53/1493 252/189 |
| 4,537,753 | A | 8/1985 | Wagner et al. | |
| 4,553,984 | A | 11/1985 | Volkamer et al. | |
| 4,780,495 | A * | 10/1988 | Lai | C08K 5/3462 544/386 |
| 5,091,425 | A * | 2/1992 | Bradbury | C07D 487/04 548/215 |
| 6,214,877 | B1 * | 4/2001 | Butera | C07C 271/28 558/170 |
| 9,670,242 | B2 * | 6/2017 | Zhang | A61P 43/00 |
| 10,566,078 | B1 * | 2/2020 | Notz | G06F 17/12 |
| 2013/0327983 | A1 * | 12/2013 | Blair | B01D 53/1493 252/184 |
| 2014/0234191 | A1 * | 8/2014 | Laroche | B01D 53/52 252/190 |
| 2015/0027055 | A1 | 1/2015 | Kortunov et al. | |
| 2015/0151240 | A1 * | 6/2015 | Laroche | B01D 53/1493 252/190 |
| 2016/0114286 | A1 * | 4/2016 | Bae | B01D 53/78 252/192 |
| 2016/0263519 | A1 * | 9/2016 | Ouimet | B01D 53/1475 |
| 2017/0080378 | A1 * | 3/2017 | Rochelle | B01D 53/96 |
| 2017/0182455 | A1 | 6/2017 | Pereira et al. | |
| 2017/0274317 | A1 * | 9/2017 | Bumb | B01D 53/1493 |
| 2018/0353896 | A1 * | 12/2018 | Mathias | B01D 53/1493 |
| 2019/0126194 | A1 * | 5/2019 | Ingram | C10L 3/104 |
| 2019/0282952 | A1 * | 9/2019 | Li | B01D 71/0211 |
| 2019/0329176 | A1 * | 10/2019 | Lu | B01D 53/1475 |
| 2020/0171423 | A1 * | 6/2020 | Amhamed | C10L 3/103 |
| 2020/0377784 | A1 * | 12/2020 | Bodnar | C10L 3/107 |
| 2021/0308619 | A1 * | 10/2021 | Bumb | B01D 53/1425 |
| 2023/0104687 | A1 * | 4/2023 | Nakano | C01B 32/50 423/228 |

FOREIGN PATENT DOCUMENTS

| | | |
|---|---|---|
| EP | 0159495 A2 | 10/1985 |
| EP | 0190434 A2 | 8/1986 |
| EP | 0202600 A2 | 11/1986 |
| EP | 0359991 A1 | 3/1990 |
| WO | 01/00271 A1 | 1/2001 |
| WO | 2011/067199 A1 | 6/2011 |
| WO | 2014/001664 A1 | 1/2014 |
| WO | 2014/001669 A1 | 1/2014 |
| WO | 2017/186466 A1 | 11/2017 |

OTHER PUBLICATIONS

International Search Report and Written Opinion received for PCT Patent Application No. PCT/EP2020/053924, mailed on Apr. 20, 2020, 9 pages.

* cited by examiner

PROCESS FOR REMOVAL OF ACID GASES FROM A FLUID STREAM WITH A LIQUID ABSORBENT COMPRISING A PIPERAZINE RING

CROSS-REFERENCE TO RELATED APPLICATIONS

This application is a national stage application (under 35 U.S.C. § 371) of PCT/EP2020/053924, filed Feb. 14, 2020, which claims benefit of European Application No. 19157704.8, filed Feb. 18, 2019, both of which are incorporated herein by reference in their entirety.

The present invention relates to a process for removal of acid gases from a fluid stream and an absorbent suitable for the absorption of acid gases from a fluid stream.

The removal of acid gases, for example $CO_2$, $H_2S$, $SO_2$, $CS_2$, HCN, COS or mercaptans, from fluid streams such as natural gas, refinery gas or synthesis gas is desirable for various reasons. Sulfur compounds in natural gas tend to form corrosive acids, in particular together with the water frequently entrained by the natural gas. For the transport of the natural gas in a pipeline or further processing in a natural gas liquefaction plant (LNG=liquefied natural gas), given limits for the sulfur-containing impurities therefore have to be observed. In addition, numerous sulfur compounds are malodorous and toxic even at low concentrations.

Carbon dioxide has to be removed from natural gas because a high concentration of $CO_2$ reduces the calorific value of the gas. Moreover, $CO_2$ in conjunction with moisture can lead to corrosion in pipes and valves.

Known processes for removing acid gases include scrubbing operations with aqueous absorbent solutions of inorganic or organic bases. When acid gases are dissolved in the absorbent, ions form with the bases. The absorbent can be regenerated by decompression to a lower pressure and/or by stripping, whereby the ionic species react in reverse and the acid gases are released and/or stripped out by means of an inert fluid, e.g., steam. After the regeneration process, the absorbent can be reused.

A process in which $CO_2$ and $H_2S$ are substantially removed is referred to as "total absorption". While removal of $CO_2$ may be necessary to avoid corrosion problems and provide the required heating value to the consumer, it is occasionally necessary or desirable to treat acid gas mixtures containing both $CO_2$ and $H_2S$ so as to remove the $H_2S$ selectively from the mixture while minimizing removal of the $CO_2$. Natural gas pipeline specifications, for example, set more stringent limits on the $H_2S$ level than on $CO_2$ since $H_2S$ is more toxic and corrosive than $CO_2$: common carrier natural gas pipeline specifications typically limit the $H_2S$ content to 4 ppmv with a more lenient limitation on the $CO_2$ at 2 vol-%. Selective $H_2S$ removal is often desirable to enrich the $H_2S$ level in the feed to a sulfur recovery unit, such as a downstream Claus plant.

Severely sterically hindered secondary amines, such as 2-(2-tert-butylaminoethoxy)ethanol (TBAEE), and tertiary amines, such as methyldiethanolamine (MDEA), exhibit kinetic selectivity for $H_2S$ over $CO_2$. Such amines are therefore suitable for the selective removal of $H_2S$ over $CO_2$ from gas mixtures comprising $CO_2$ and $H_2S$ and are generally utilized as aqueous mixtures. These amines do not react directly with $CO_2$; instead, $CO_2$ is reacted in a slow reaction with the amine and with water to give a bicarbonate ion. The reaction kinetics allow $H_2S$ to react directly, more rapidly, with the amine groups of the sorbent to form a hydrosulfide ion in aqueous solution.

US 2015/0027055 A1 describes a process for selectively removing $H_2S$ from a $CO_2$-containing gas mixture by means of an absorbent comprising sterically hindered, terminally etherified alkanolamines.

US 2017/182455 A1 describes a process for selectively separating $H_2S$ from a gas mixture which also comprises $CO_2$, wherein a stream of the gas mixture is contacted with an absorbent solution comprising one or more amines, alkanolamines, hindered alkanolamines, capped alkanolamines, or mixtures thereof.

WO 2014/001664 A1 describes amino alkyl substituted morpholine derivatives and their use in the removal of acid gases.

DE 40 272 49 A1 describes compounds comprising a heterocyclic moiety with two nitrogen atoms and their use in selectively removing inorganic and organic sulfur compounds from gas streams.

WO 2014/001669 A1 describes absorbent solutions comprising aminoalkylpiperazine derivatives and their use in a method of removing acid compound from a gaseous effluent. As shown in the examples and comparative examples that follow, these compounds are prone to deterioration, presumably due to the lack of steric hindrance of the amino moiety outside the piperazine ring.

A BRIEF DESCRIPTION OF THE FIGURES

Figure 1:
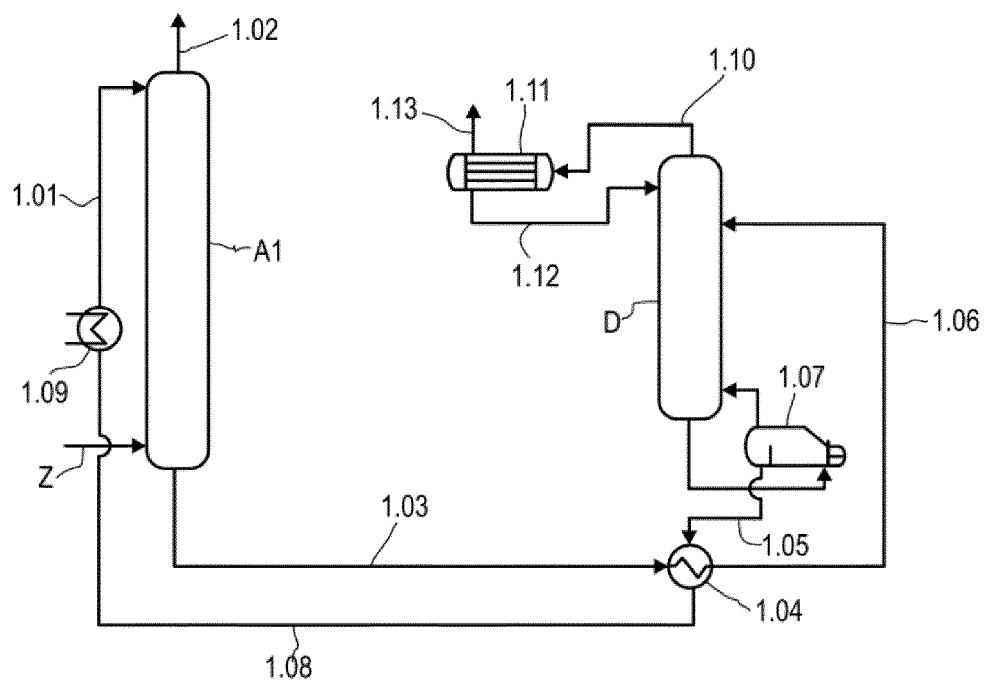
FIG. 1 is a schematic diagram of a plant suitable for performing the process of the invention.

It is an object of the invention to provide further absorbents and processes suitable for removing acid gases from fluid streams. The absorbents are to be useful for the selective removal of hydrogen sulfide from fluid streams. The absorbents are to have high acid gas loading capacity, high stability, and low volatility.

The object is achieved by a process for removal of acid gases from fluid stream, wherein a fluid stream is brought into contact with an absorbent to obtain a treated fluid stream and a laden absorbent, the absorbent comprising a diluent and a compound of the general formula (I)

$$R^1-N\underset{}{\underbrace{\phantom{XXX}}}N-\underset{H}{\overset{R^2}{\underset{|}{C}}}-(CH_2)_n-\underset{H}{\overset{R^3}{\underset{|}{C}}}-N\underset{R^5,}{\overset{R^4}{\diagup}} \quad (I)$$

wherein
$R^1$ is selected from $C_1$-$C_8$-alkyl and $C_2$-$C_8$-hydroxyalkyl;
$R^2$ is selected from hydrogen and $C_1$-$C_8$-alkyl;
$R^3$ is selected from hydrogen and $C_1$-$C_8$-alkyl;
$R^4$ is selected from hydrogen and $C_1$-$C_8$-alkyl;
$R^5$ is $C_1$-$C_8$-alkyl;
with the proviso that at least one of the following conditions (i) and (ii) is met:
(i) $R^5$ is $C_3$-$C_8$-alkyl bound to the nitrogen atom via a secondary or tertiary carbon atom;
(ii) when $R^4$ is hydrogen, $R^3$ is $C_1$-$C_8$-alkyl; or
when $R^4$ is $C_1$-$C_8$-alkyl, at least one of $R^2$ and $R^3$ is $C_1$-$C_8$-alkyl;

and n is an integer from 0 to 6.

It was found that such an absorbent favorably displays high acid gas loading capacity, high stability, and low volatility.

Further, the invention relates to an absorbent for the absorption of acid gases from a fluid stream as described above, and to the use of a compound of the general formula (I) for removal of acid gases from a fluid stream. It is understood that embodiments described herein relate to all aspects of the invention, i.e., to the absorbent, the use of the compound of formula (I), and the process, where applicable.

The compound of the general formula (I) comprises two tertiary amino groups, the nitrogen atoms of which are part of a piperazine ring structure. Attached to the piperazine ring structure is an alkylene moiety terminated by an amino group which is either a tertiary amino group or a sterically hindered secondary amino group. When the compound of the general formula (I) comprises a secondary amino group, i.e. when $R^4$ is hydrogen, $R^3$ is $C_1$-$C_8$-alkyl and/or $R^5$ is $C_3$-$C_8$-alkyl bound to the nitrogen atom via a secondary or tertiary carbon atom. Thus, the nitrogen atom in the secondary amino group has at least one secondary or tertiary carbon atom directly adjacent and is therefore sterically hindered.

Since all amino functions of the compound of the general formula (I) are either tertiary amino groups or sterically hindered secondary amino groups, the compounds show kinetic selectivity for $H_2S$ removal.

$R^1$ is selected from $C_1$-$C_8$-alkyl and $C_2$-$C_8$-hydroxyalkyl. $R^1$ is preferably $C_1$-$C_8$-alkyl, more preferably $C_1$-$C_5$-alkyl. $R^1$ is most preferably selected from methyl, ethyl, n-propyl and n-butyl, especially methyl.

$R^2$ is selected from hydrogen and $C_1$-$C_8$-alkyl. $R^2$ is preferably hydrogen. In one embodiment, $R^2$ is $C_1$-$C_5$-alkyl, such as methyl, ethyl, n-propyl or n-butyl, especially methyl.

$R^3$ is selected from hydrogen and $C_1$-$C_8$-alkyl. $R^3$ is preferably hydrogen. In one embodiment, $R^3$ is $C_1$-$C_5$-alkyl, such as methyl, ethyl, n-propyl or n-butyl, especially methyl.

When $R^2$ is $C_1$-$C_8$-alkyl, it is preferred that $R^3$ is hydrogen. When $R^3$ is $C_1$-$C_8$-alkyl, it is preferred that $R^2$ is hydrogen. In one embodiment, $R^2$ is methyl and $R^3$ is hydrogen. In another embodiment, $R^2$ is hydrogen and $R^3$ is methyl. In a preferred embodiment, both $R^2$ and $R^3$ are hydrogen.

$R^4$ is selected from hydrogen and $C_1$-$C_8$-alkyl. $R^4$ is preferably hydrogen. Alternatively, $R^4$ may be $C_1$-$C_5$-alkyl, such as methyl, ethyl, n-propyl or n-butyl, especially methyl.

$R^5$ is $C_1$-$C_8$-alkyl. $R^5$ may for example be linear $C_1$-$C_5$-alkyl, such as methyl, ethyl, n-propyl or n-butyl, especially methyl, or $R^5$ may for example be $C_3$-$C_8$-alkyl bound to the nitrogen atom via a secondary or tertiary carbon atom, such as $C_3$-$C_5$-alkyl bound to the nitrogen atom via a secondary or tertiary carbon atom, for example isopropyl (—CH(CH$_3$)$_2$), tert-butyl (—C(CH$_3$)$_3$) and tert-pentyl (—C(CH$_3$)$_2$—CH$_2$—CH$_3$), especially tert-butyl.

In the compounds of the general formula (I), at least one of the following conditions (i) and (ii) is met: (i) $R^5$ is $C_3$-$C_8$-alkyl bound to the nitrogen atom via a secondary or tertiary carbon atom; (ii) when $R^4$ is hydrogen, $R^3$ is $C_1$-$C_8$-alkyl; or when $R^4$ is $C_1$-$C_8$-alkyl, at least one of $R^2$ and $R^3$ is $C_1$-$C_8$-alkyl. When condition (i) applies, $R^5$ is most preferably selected from isopropyl, tert-butyl and tert-pentyl, especially tert-butyl.

n is an integer from 0 to 6, i.e. 0, 1, 2, 3, 4, 5 or 6. n is preferably an integer from 0 to 3, i.e. 0, 1, 2 or 3. Most preferably, n is 0 or 1.

The term "alkyl" is understood to include both branched and straight-chain saturated aliphatic hydrocarbon groups having the specified number of carbon atoms. This also applies to the alkyl groups comprised in hydroxyalkyl substituents.

In one embodiment, $R^1$ is $C_1$-$C_5$-alkyl;

$R^2$ is selected from hydrogen and $C_1$-$C_5$-alkyl;

$R^3$ is selected from hydrogen and $C_1$-$C_5$-alkyl;

$R^4$ is selected from hydrogen and $C_1$-$C_5$-alkyl;

$R^5$ is $C_1$-$C_5$-alkyl;

with the proviso that at least one of the following conditions (i') and (ii') is met:

(i') $R^5$ is $C_3$-$C_5$-alkyl bound to the nitrogen atom via a secondary or tertiary carbon atom;

(ii') when $R^4$ is hydrogen, $R^3$ is $C_1$-$C_5$-alkyl; or when $R^4$ is $C_1$-$C_5$-alkyl, at least one of $R^2$ and $R^3$ is $C_1$-$C_5$-alkyl;

and n is an integer from 1 to 4;

for instance, $R^1$ is $C_1$-$C_5$-alkyl;

$R^2$ is hydrogen;

$R^3$ is hydrogen;

$R^4$ is $C_1$-$C_5$-alkyl;

$R^5$ is selected from isopropyl, tert-butyl or tert-pentyl, preferably tert-butyl; and n is 0 or 1.

or, preferably, $R^1$ is $C_1$-$C_5$-alkyl;

$R^2$ is hydrogen;

$R^3$ is hydrogen;

$R^4$ is hydrogen;

$R^5$ is selected from isopropyl, tert-butyl or tert-pentyl, preferably tert-butyl; and n is 0 or 1.

Examples of compounds of the general formula (I) include:

2-methyl-2-(4-methylpiperazin-1-yl)ethyl-dimethylamine;

3-methyl-3-(4-methylpiperazin-1-yl)propyl-dimethylamine;

4-methyl-4-(4-methylpiperazin-1-yl)butyl-dimethylamine;

5-methyl-5-(4-methylpiperazin-1-yl)pentyl-dimethylamine;

N-methyl-1-methyl-2-(4-methylpiperazin-1-yl)ethylamine;

N-methyl-1-methyl-3-(4-methylpiperazin-1-yl)propylamine;

N-methyl-1-methyl-4-(4-methylpiperazin-1-yl)butylamine;

N-methyl-1-methyl-5-(4-methylpiperazin-1-yl)pentylamine;

1-methyl-2-(4-methylpiperazin-1-yl)ethyl-dimethylamine;

1-methyl-3-(4-methylpiperazin-1-yl)propyl-dimethylamine;

1-methyl-4-(4-methylpiperazin-1-yl)butyl-dimethylamine;

1-methyl-5-(4-methylpiperazin-1-yl)pentyl-dimethylamine;

N-methyl-N-isopropyl-1-methyl-2-(4-methylpiperazin-1-yl)ethylamine;

N-methyl-N-isopropyl-2-methyl-2-(4-methylpiperazin-1-yl)ethylamine;

N-methyl-N-tert-butyl-1-methyl-2-(4-methylpiperazin-1-yl)ethylamine;

N-methyl-N-tert-butyl-2-methyl-2-(4-methylpiperazin-1-yl)ethylamine;

N-methyl-N-isopropyl-1-methyl-3-(4-methylpiperazin-1-yl)propylamine;

N-methyl-N-isopropyl-3-methyl-3-(4-methylpiperazin-1-yl)propylamine;

N-methyl-N-tert-butyl-1-methyl-3-(4-methylpiperazin-1-yl)propylamine;

N-methyl-N-tert-butyl-3-methyl-3-(4-methylpiperazin-1-yl)propylamine;
N-methyl-N-isopropyl-2-(4-methylpiperazin-1-yl)ethylamine;
N-methyl-N-isopropyl-3-(4-methylpiperazin-1-yl)propylamine;
N-methyl-N-isopropyl-4-(4-methylpiperazin-1-yl)butylamine;
N-methyl-N-isopropyl-5-(4-methylpiperazin-1-yl)pentylamine;
N-methyl-N-tert-butyl-2-(4-methylpiperazin-1-yl)ethylamine;
N-methyl-N-tert-butyl-3-(4-methylpiperazin-1-yl)propylamine;
N-methyl-N-tert-butyl-4-(4-methylpiperazin-1-yl)butylamine;
N-methyl-N-tert-butyl-5-(4-methylpiperazin-1-yl)pentylamine;
2-(4-methylpiperazin-1-yl)ethyl-isopropylamine;
3-(4-methylpiperazin-1-yl)propyl-isopropylamine;
4-(4-methylpiperazin-1-yl)butyl-isopropylamine;
5-(4-methylpiperazin-1-yl)pentyl-isopropylamine;
2-(4-methylpiperazin-1-yl)ethyl-tert-butylamine;
3-(4-methylpiperazin-1-yl)propyl-tert-butylamine;
4-(4-methylpiperazin-1-yl)butyl-tert-butylamine; and
5-(4-methylpiperazin-1-yl)pentyl-tert-butylamine.

Preferably, the compound of the general formula (I) is selected from 2-methyl-2-(4-methylpiperazin-1-yl)ethyl-dimethylamine, N-methyl-1-methyl-2-(4-methylpiperazin-1-yl)ethylamine, 3-(4-methylpiperazin-1-yl)propyl-tert-butylamine (TBAP-MPIP) and 2-(4-methyl-piperazin-1-yl)ethyl-tert-butylamine (TBAE-MPIP), most preferably from 3-(4-methylpiperazin-1-yl)propyl-tert-butylamine (TBAP-MPIP) and 2-(4-methyl-piperazin-1-yl)ethyl-tert-butylamine (TBAE-MPIP).

The absorbent preferably comprises a total amount of 10% to 70% by weight, more preferably 15% to 65% by weight and most preferably 20% to 60% by weight of the compound of the general formula (I), based on the total weight of the absorbent.

Compounds of the general formula (I) are known as such or can be synthesized by reacting an alcohol of formula (Ia)

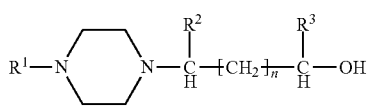
(Ia)

with an amine $HNR^4R^5$ in the presence of a suitable amination catalyst at elevated temperature and pressure in the presence of hydrogen. The amine may be a primary amine (wherein $R^4$ is hydrogen), for example tert-butylamine, or a secondary amine (wherein $R^4$ is $C_1$-$C_8$-alkyl), for example dimethylamine or methyl-tert-butylamine.

Preferably, the amine $HNR^4R^5$ is used in molar excess over the molar amount of the alcohol of formula (Ia) during the reaction. In a preferred embodiment, the molar amount of the amine exceeds the molar amount of the alcohol at the start of the reaction by 5 to 5,000 mol-%, preferably 50 to 1,000 mol-%, based on the amount of the alcohol.

Preferably, the reaction is carried out in the presence of a hydrogenation/dehydrogenation catalyst, for example in the presence of a copper-containing hydro-genation/dehydrogenation catalyst. The catalyst may be applied to a support, for example an alumina support.

In one embodiment, a supported copper-, nickel- and cobalt-containing hydrogenation/dehydrogenation catalyst is used, wherein the catalytically active material of the catalyst, before the reduction thereof with hydrogen, comprises oxygen compounds of aluminum, of copper, of nickel and of cobalt, and in the range of 0.2 to 5.0% by weight of oxygen compounds of tin, calculated as SnO. In a preferred embodiment, a catalyst according to the catalysts claimed in WO 2011/067199 is used, particularly a catalyst according to WO 2011/067199, example 5.

The catalyst load may be varied in the range of 0.01 to 2 kg/(L·h), preferably in the range of 0.1 to 1.0 kg/(L·h), and in an especially preferred embodiment in the range of 0.2 to 0.8 kg/(L·h) of alcohol of formula (Ia).

In a preferred embodiment, the reaction is carried out at a temperature of 150 to 260° C. In an especially preferred embodiment, the reaction is carried out at a temperature of 170 to 240° C., such as 170 to 200° C.

The reaction may be carried out at pressures from 5 to 300 bar, in liquid or vapor phase. In a preferred embodiment, the reaction is carried out at a pressure of 60 to 220 bar. Here and throughout the description, all pressures are absolute pressures (bar absolute), unless noted otherwise.

The reaction may be carried out using stirred tank reactors, fixed bed tube reactors and multitube reactors. It may be carried out in batch, semi-batch and continuous mode and with and without recycling of the crude reaction mixture. In a preferred embodiment, the reaction is carried out in continuous mode in a fixed bed tube reactor.

In one embodiment, excess amine $HNR^4R^5$ is separated from the product of the reaction by one-step distillation. The term "one-step distillation" is understood to mean a distillation with only a single separating stage, as is the case in a simple distillation setup where vapor generated in a reboiler is immediately channeled into a condenser. Contrarily, rectification columns, e.g., have several separating stages and represent a fractional distillation. In another embodiment, excess amine $HNR^4R^5$ is separated from the product of the reaction by fractional distillation. Preferably, the separated excess amine is recycled to the further production of the amine (I).

Besides the amine (I), the alcohol (Ia) and the amine $HNR^4R^5$, the reaction product contains several other substances. Usually, the reaction product contains water and side-products, such as ether derivatives of the alcohol (Ia).

In a preferred embodiment, water and side-products are separated from the product of the reaction. In an especially preferred embodiment, water and side-products, as well as excess amine still remaining in the reaction product after the distillation described above, are removed from the reaction product by a further distillation step, preferably a one-step distillation step. This step is preferably carried out at a pressure of about 90 mbar. Any suited reboiler can be applied for this step. A falling film evaporator or thin film evaporator can be used. Particularly, thin film evaporation using a "Sambay" type evaporator may be applied and the generated gas is condensed at room temperature.

After the work-up steps, the obtained product may be mixed with a diluent in order to obtain an absorbent of the invention. Further substances, as described above, may be added.

Alternatively, after the work-up steps, the obtained product may be transported to a site of utilization of acid gas absorbents, such as a gas scrubbing plant, and mixed with a diluent on-site to obtain an absorbent of the invention. Further substances, as described above, may be added on-site.

The absorbent comprises a diluent. Preferably, the diluent is selected from water, organic solvents, preferably water-miscible organic solvents, and combinations thereof. The absorbent preferably comprises a total amount of 20% to 90% by weight, more preferably 30 to 80% by weight and most preferably 40 to 65% by weight of diluent, based on the total weight of the absorbent.

In a preferred embodiment, the diluent comprises water. It may, however, be desirable to limit the water content of the absorbent, for example to a maximum of 20% by weight, alternatively to a maximum of 10% by weight, preferably to a maximum of 5% by weight, or a maximum of 2% by weight. Limiting the water content of the absorbent may improve the selectivity of the absorbent for $H_2S$ over $CO_2$.

The organic solvent is preferably selected from:

$C_4$-$C_{10}$ alcohols such as n-butanol, n-pentanol and n-hexanol;

ketones such as cyclohexanone;

esters such as ethyl acetate and butyl acetate;

lactones such as γ-butyrolactone, δ-valerolactone and ε-caprolactone;

amides such as tertiary carboxamides, for example N,N-dimethylformamide; or N-formylmorpholine and N-acetylmorpholine;

lactams such as γ-butyrolactam, δ-valerolactam and ε-caprolactam and N-methyl-2-pyrrolidone (NMP);

sulfones such as sulfolane;

sulfoxides such as dimethyl sulfoxide (DMSO);

glycols such as ethylene glycol (EG) and propylene glycol;

polyalkylene glycols such as diethylene glycol (DEG) and triethylene glycol (TEG);

di- or mono($C_1$-$C_4$-alkyl ether) glycols such as ethylene glycol monomethyl or dimethyl ether;

di- or mono($C_1$-$C_4$-alkyl ether) polyalkylene glycols such as diethylene glycol dimethyl ether, dipropylene glycol monomethyl ether and triethylene glycol dimethyl ether;

cyclic ureas such as N,N-dimethylimidazolidin-2-one and dimethylpropyleneurea (DMPU);

thioalkanols such as ethylenedithioethanol, thiodiethylene glycol (thiodiglycol, TDG) and methylthioethanol;

and mixtures thereof.

More preferably, the organic solvent is selected from sulfones, glycols and polyalkylene glycols. Most preferably, the organic solvent is selected from sulfones. A preferred organic solvent is sulfolane.

In one embodiment, the absorbent comprises a tertiary amine or severely sterically hindered primary amine and/or severely sterically hindered secondary amine other than the compounds of the general formula (I). Severe steric hindrance is understood to mean a tertiary carbon atom directly adjacent to a primary or secondary nitrogen atom. In this embodiment, the absorbent comprises the tertiary amine or severely sterically hindered primary or secondary amine other than the compounds of the general formula (I) generally in an amount of 5% to 50% by weight, preferably 10% to 40% by weight and more preferably 20% to 40% by weight, based on the total weight of the absorbent.

The suitable tertiary amines especially include:

1. Tertiary alkanolamines such as
bis(2-hydroxyethyl)methylamine (methyldiethanolamine, MDEA), tris(2-hydroxy-ethyl)amine (triethanolamine, TEA), tributanolamine, 2-diethylaminoethanol (diethylethanolamine, DEEA), 2-dimethylaminoethanol (dimethylethanolamine, DMEA), 3-dimethylamino-1-propanol (N,N-dimethylpropanolamine), 3-diethylamino-1-propanol, 2-diisopropylaminoethanol (DIEA), N,N-bis(2-hydroxypropyl)methylamine (methyldiisopropanolamine, MDIPA);

2. Tertiary amino ethers such as 3-methoxypropyldimethylamine;

3. Tertiary polyamines, for example bis-tertiary diamines such as
N,N,N',N'-tetramethylethylenediamine, N,N-diethyl-N',N'-dimethylethylenediamine, N,N,N',N'-tetraethylethylenediamine, N,N,N',N'-tetramethyl-1,3-propanediamine (TMPDA), N,N,N',N'-tetraethyl-1,3-propanediamine (TEPDA), N,N,N',N'-tetramethyl-1,6-hexanediamine, N,N-dimethyl-N',N'-diethylethylenediamine (DMDEEDA), 1-dimethylamino-2-dimethylaminoethoxyethane (bis[2-(dimethylamino)ethyl] ether), 1,4-diazabicyclo[2.2.2]octane (TEDA), tetramethyl-1,6-hexanediamine;

and mixtures thereof.

Tertiary alkanolamines, i.e., amines having at least one hydroxyalkyl group bonded to the nitrogen atom, are generally preferred. Particular preference is given to methyldiethanolamine (MDEA).

The suitable severely sterically hindered primary or secondary amines (i.e., amines having a tertiary carbon atom directly adjacent to a primary or secondary nitrogen atom) other than the compounds of the general formula (I) especially include:

1. Severely sterically hindered secondary alkanolamines such as
2-(2-tert-butylaminoethoxy)ethanol (TBAEE), 2-(2-tert-butylamino)propoxyethanol, 2-(2-tert-amylaminoethoxy)ethanol, 2-(2-(1-methyl-1-ethylpropylamino)ethoxy)ethanol, 2-(tert-butylamino)ethanol, 2-tert-butylamino-1-propanol, 3-tert-butylamino-1-propanol, 3-tert-butylamino-1-butanol, and 3-aza-2,2-dimethylhexane-1,6-diol, 2-N-methylamino-propan-1-ol, 2-N-methylamino-2-methylpropan-1-ol;

2. Severely sterically hindered primary alkanolamines such as
2-amino-2-methylpropanol (2-AMP); 2-amino-2-ethylpropanol; and 2-amino-2-propylpropanol;

3. Severely sterically hindered amino ethers such as 1,2-bis(tert-butylaminoethoxy)ethane, bis(tert-butylaminoethyl) ether;

and mixtures thereof.

Severely sterically hindered secondary alkanolamines are generally preferred. Particular preference is given to 2-(2-tert-butylaminoethoxy)ethanol and 2-(2-tert-butylaminoethoxyethoxy)ethanol.

Although the compounds of the general formula (I) show intrinsic kinetic selectivity for $H_2S$ removal it may in certain embodiments be desirable to remove $CO_2$ along $H_2S$. Removal of $CO_2$ can be facilitated by incorporation of an activator in the absorbent.

In one embodiment, the absorbent comprises at least one activator selected from a sterically unhindered primary amine and/or a sterically unhindered secondary amine. A sterically unhindered primary amine is understood to mean compounds having primary amino groups to which only a primary or a secondary carbon atom is bonded. A sterically unhindered secondary amine is understood to mean compounds having secondary amino groups to which only primary carbon atoms are bonded. Sterically unhindered primary amines or sterically unhindered secondary amines act as strong activators of $CO_2$ absorption. Accordingly, the presence of an activator may be desirable in applications directed at the non-selective removal of acid gases or applications in which the removal of $CO_2$ is especially important.

The activator preferably does not comprise acidic groups such as, in particular, phosphonic acid, sulfonic acid and/or carboxylic acid groups.

The activator is, for example, selected from
alkanolamines such as monoethanolamine (MEA), diethanolamine (DEA), ethylaminoethanol, 1-amino-2-methylpropan-2-ol, 2-amino-1-butanol, 2-(2-amino-ethoxy)ethanol and 2-(2-aminoethoxy)ethanamine,
polyamines such as hexamethylenediamine, 1,4-diaminobutane, 1,3-diaminopropane, 3-(methylamino)propylamine (MAPA), N-(2-hydroxyethyl)ethylenediamine, 3-(dimethyl-amino)propylamine (DMAPA), 3-(diethylamino)propylamine, N,N'-bis(2-hydroxyethyl)-ethylenediamine,
5-, 6- or 7-membered saturated heterocycles having at least one NH group in the ring, which may comprise one or two further heteroatoms selected from nitrogen and oxygen in the ring, such as piperazine, 2-methylpiperazine, N-methylpiperazine, N-ethyl-piperazine, N-(2-hydroxyethyl)piperazine, N-(2-aminoethyl)piperazine, homopiperazine, piperidine and morpholine.

Particular preference is given to 5-, 6- or 7-membered saturated heterocycles having at least one NH group in the ring, which may comprise one or two further heteroatoms selected from nitrogen and oxygen in the ring. Very particular preference is given to piperazine.

On the other hand, where $H_2S$ selectivity is desired, the absorbent preferably does not comprise any sterically unhindered primary amine or sterically unhindered secondary amine. Since sterically unhindered primary amines or sterically unhindered secondary amines act as strong activators of $CO_2$ absorption, their presence in the absorbent can result in a loss of the $H_2S$ selectivity of the absorbent. Accordingly, in applications where a high $H_2S$ selectivity is desirable, an absorbent essentially free of such compounds is preferable.

In one embodiment, the absorbent comprises an acid. The acid helps to regenerate the absorbent to low loadings and enhance the efficiency of the process. Protonation equilibria form between the acid and the compound of the general formula (I). The position of the equilibria is temperature-dependent, and the equilibrium is shifted at higher temperatures toward the free oxonium ion and/or the amine salt having the lower enthalpy of protonation. At relatively low temperatures as prevail in the absorption step, the higher pH promotes efficient acid gas absorption, whereas, at relatively high temperatures as prevail in the desorption step, the lower pH supports the release of the absorbed acid gases.

The acid preferably has a $pK_A$ of less than 6, especially less than 5, measured at 25° C. In the case of acids having more than one dissociation stage and accordingly more than one $pK_A$, this requirement is met where one of the $pK_A$ values is within the range specified. The acid is suitably selected from protic acids (Brønsted acids).

The acid is preferably added in such an amount that the pH of the aqueous solution measured at 120° C. is 7.9 to less than 9.5, preferably 8.0 to less than 8.8, more preferably 8.0 to less than 8.5, most preferably 8.0 to less than 8.2.

The amount of acid, in one embodiment, is 0.1% to 5.0% by weight, preferably 0.2% to 4.5% by weight, more preferably 0.5% to 4.0% by weight and most preferably 1.0% to 2.5% by weight, based on the total weight of the absorbent.

The acid is selected from organic and inorganic acids. Suitable organic acids comprise, for example, phosphonic acids, sulfonic acids, carboxylic acids and amino acids. In particular embodiments, the acid is a polybasic acid.

Suitable Acids are, for Example,
mineral acids such as hydrochloric acid, sulfuric acid, amidosulfuric acid, phosphoric acid, partial esters of phosphoric acid, for example mono- and dialkyl phosphates and mono- and diaryl phosphates such as tridecyl phosphate, dibutyl phosphate, diphenyl phosphate and bis(2-ethylhexyl) phosphate; boric acid;

carboxylic acids, for example saturated aliphatic monocarboxylic acids such as formic acid, acetic acid, propionic acid, butyric acid, isobutyric acid, valeric acid, isovaleric acid, pivalic acid, caproic acid, n-heptanoic acid, caprylic acid, 2-ethylhexanoic acid, pelargonic acid, caproic acid, neodecanoic acid, undecanoic acid, lauric acid, tridecanoic acid, myristic acid, pentadecanoic acid, palmitic acid, margaric acid, stearic acid, isostearic acid, arachic acid, behenic acid; saturated aliphatic polycarboxylic acids such as oxalic acid, malonic acid, succinic acid, glutaric acid, adipic acid, pimelic acid, suberic acid, azelaic acid, sebacic acid, dodecanedioic acid; cycloaliphatic mono- and polycarboxylic acids such as cyclohexanecarboxylic acid, hexahydrophthalic acid, tetrahydrophthalic acid, resin acids, naphthenic acids; aliphatic hydroxycarboxylic acids such as glycolic acid, lactic acid, mandelic acid, hydroxybutyric acid, tartaric acid, malic acid, citric acid; halogenated aliphatic carboxylic acids such as trichloroacetic acid or 2-chloropropionic acid; aromatic mono- and polycarboxylic acids such as benzoic acid, salicylic acid, gallic acid, the positionally isomeric toluic acids, methoxybenzoic acids, chlorobenzoic acids, nitrobenzoic acids, phthalic acid, terephthalic acid, isophthalic acid; technical carboxylic acid mixtures, for example Versatic acids;

sulfonic acids such as methylsulfonic acid, butylsulfonic acid, 3-hydroxypropylsulfonic acid, sulfoacetic acid, benzenesulfonic acid, p-toluenesulfonic acid, p-xylenesulfonic acid, 4-dodecylbenzenesulfonic acid, 1-naphthalenesulfonic acid, dinonylnaphthalene-sulfonic acid and dinonylnaphthalenedisulfonic acid, trifluoromethyl- or nonafluoro-n-butylsulfonic acid, camphorsulfonic acid, 2-(4-(2-hydroxyethyl)-1-piperazinyl)-ethanesulfonic acid (HEPES);

organic phosphonic acids, for example phosphonic acids of the formula (A-I)

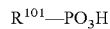

$$R^{101}\text{—}PO_3H \qquad (A\text{-}I)$$

in which $R^{101}$ is $C_{1\text{-}18}$-alkyl optionally substituted by up to four substituents independently selected from carboxyl, carboxamido, hydroxyl and amino.

These include alkylphosphonic acids such as methylphosphonic acid, propylphosphonic acid, 2-methylpropylphosphonic acid, t-butylphosphonic acid, n-butylphosphonic acid, 2,3-dimethylbutylphosphonic acid, octylphosphonic acid; hydroxyalkylphosphonic acids such as hydroxymethylphosphonic acid, 1-hydroxyethylphosphonic acid, 2-hydroxyethylphosphonic acid; arylphosphonic acids such as phenylphosphonic acid, tolylphosphonic acid, xylylphosphonic acid, amino-alkylphosphonic acids such as aminomethylphosphonic acid, 1-aminoethylphosphonic acid, 1-dimethylaminoethylphosphonic acid, 2-aminoethylphosphonic acid, 2-(N-methylamino)ethylphosphonic acid, 3-aminopropylphosphonic acid, 2-aminopropylphosphonic acid, 1-aminopropylphosphonic acid, 1-aminopropyl-2-chloropropylphosphonic acid, 2-aminobutylphosphonic acid, 3-aminobutylphosphonic acid, 1-aminobutylphosphonic acid, 4-aminobutylphosphonic acid, 2-aminopentylphosphonic acid, 5-aminopentylphosphonic acid, 2-aminohexylphosphonic acid, 5-aminohexylphosphonic acid, 2-aminooctylphosphonic acid, 1-aminooctylphosphonic acid, 1-aminobutylphosphonic acid;

amidoalkylphosphonic acids such as 3-hydroxymethylamino-3-oxopropylphosphonic acid; and phosphonocarboxylic acids such as 2-hydroxyphosphonoacetic acid and 2-phosphonobutane-1,2,4-tricarboxylic acid;

phosphonic acids of the formula (A-II)

(A-II)

in which $R^{102}$ is H or $C_{1-6}$-alkyl, Q is H, OH or $NR^{103}{}_2$ and $R^{103}$ is H or $CH_2PO_3H2$, such as 1-hydroxyethane-1,1-diphosphonic acid;

phosphonic acids of the formula (A-III)

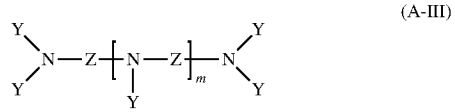

(A-III)

in which Z is $C_{2-6}$-alkylene, cycloalkanediyl, phenylene, or $C_{2-6}$-alkylene interrupted by cycloalkanediyl or phenylene, Y is $CH_2PO_3H_2$ and m is 0 to 4, such as ethylenediaminetetra(methylenephosphonic acid), diethylenetriaminepenta(methylenephosphonic acid) and bis(hexamethylene)triaminepenta(methylenephosphonic acid);

phosphonic acids of the formula (A-IV)

(A-IV)

in which $R^{104}$ is $C_{1-6}$-alkyl, $C_{2-6}$-hydroxyalkyl or $R^{105}$, and $R^{105}$ is $CH_2PO_3H_2$, such as nitrilotris(methylenephosphonic acid) and 2-hydroxyethyliminobis(methylenephosphonic acid);

aminocarboxylic acids having tertiary amino groups or amino groups having at least one secondary or tertiary carbon atom immediately adjacent to the amino group, such as α-amino acids having tertiary amino groups or amino groups having at least one secondary or tertiary carbon atom immediately adjacent to the amino group, such as N,N-dimethylglycine (dimethylaminoacetic acid), N,N-diethylglycine, alanine (2-aminopropionic acid), N-methylalanine (2-(methylamino)propionic acid), N,N-dimethylalanine, N-ethylalanine, 2-methylalanine (2-aminoisobutyric acid), leucine (2-amino-4-methylpentan-1-oic acid), N-methylleucine, N,N-dimethylleucine, isoleucine (1-amino-2-methylpentanoic acid), N-methylisoleucine, N,N-dimethylisoleucine, valine (2-aminoisovaleric acid), α-methylvaline (2-amino-2-methylisovaleric acid), N-methylvaline (2-methylaminoisovaleric acid), N,N-dimethylvaline, proline (pyrrolidine-2-carboxylic acid), N-methylproline, N-methylserine, N,N-dimethylserine, 2-(methylamino)isobutyric acid, piperidine-2-carboxylic acid, N-methylpiperidine-2-carboxylic acid, β-amino acids having tertiary amino groups or amino groups having at least one secondary or tertiary carbon atom immediately adjacent to the amino group, such as 3-dimethylaminopropionic acid, N-methyliminodipropionic acid, N-methylpiperidine-3-carboxylic acid, γ-amino acids having tertiary amino groups or amino groups having at least one secondary or tertiary carbon atom immediately adjacent to the amino group, such as 4-dimethylaminobutyric acid, or aminocarboxylic acids having tertiary amino groups or amino groups having at least one secondary or tertiary carbon atom immediately adjacent to the amino group, such as N-methylpiperidine-4-carboxylic acid.

Among the inorganic acids, preference is given to phosphoric acid and sulfuric acid, especially phosphoric acid.

Among the carboxylic acids, preference is given to formic acid, acetic acid, benzoic acid, succinic acid and adipic acid.

Among the sulfonic acids, preference is given to methanesulfonic acid, p-toluenesulfonic acid and 2-(4-(2-hydroxyethyl)-1-piperazinyl)ethanesulfonic acid (HEPES).

Among the phosphonic acids, preference is given to 2-hydroxyphosphonoacetic acid, 2-phosphonobutane-1,2,4-tricarboxylic acid, 1-hydroxyethane-1,1-diphosphonic acid, ethylenediaminetetra(methylenephosphonic acid), diethylenetriaminepenta(methylenephosphonic acid), bis(hexamethylene)triaminepenta(methylenephosphonic acid) (HDTMP) and nitrilotris(methylenephosphonic acid), among which 1-hydroxyethane-1,1-diphosphonic acid is particularly preferred.

Among the aminocarboxylic acids having tertiary amino groups or amino groups having at least one secondary or tertiary carbon atom immediately adjacent to the amino group, preference is given to N,N-dimethylglycine and N-methylalanine.

More preferably, the acid is an inorganic acid.

The absorbent may also comprise additives such as corrosion inhibitors, enzymes, antifoams, etc. In general, the amount of such additives is in the range from about 0.005% to 3%, based on the total weight of the absorbent.

In the process for removal of acid gases from a fluid stream, the fluid stream is brought into contact with an absorbent as defined in any of the embodiments described above, wherein a treated fluid stream and a laden absorbent are obtained.

In one embodiment, the process is a process for selective removal of hydrogen sulfide over carbon dioxide from a fluid stream. In the present context, "selectivity for hydrogen sulfide over carbon dioxide" is understood to mean the value of the following quotient:

$$\frac{\frac{mol(H_2S)}{mol(CO_2)} \text{ (liquid phase)}}{\frac{mol(H_2S)}{mol(CO_2)} \text{ (gas phase)}}$$

where $$\frac{mol(H_2S)}{mol(CO_2)} \text{ (liquid phase)}$$

is the molar $H_2S/CO_2$ ratio in a liquid phase which is in contact with a gas phase and $$\frac{mol(H_2S)}{mol(CO_2)} \text{ (gas phase)}$$

is the molar $H_2S/CO_2$ ratio in the gas phase. In a standard gas scrubbing process, the liquid phase is the laden absorbent at the bottom of the absorber and the gas phase is the fluid stream to be treated.

A process is understood to be selective for $H_2S$ over $CO_2$ when the value of the above quotient is greater than 1. In case of a process for selective removal of hydrogen sulfide over carbon dioxide from a fluid stream, the selectivity for hydrogen sulfide over carbon dioxide is preferably at least 1.1, even more preferably at least 2 and most preferably at least 4, for example at least 6.

The absorbent of the invention is suitable for treatment of all kinds of fluids. Fluids are firstly gases such as natural gas, synthesis gas, coke oven gas, cracking gas, coal gasification gas, cycle gas, landfill gases and combustion gases, and secondly liquids that are essentially immiscible with the absorbent, such as LPG (liquefied petroleum gas) or NGL (natural gas liquids). The process of the invention is particularly suitable for treatment of hydrocarbonaceous fluid streams, especially hydrocarbonaceous gas streams, such as natural gas streams. The hydrocarbons present are, for example, aliphatic hydrocarbons such as $C_1$-$C_4$ hydrocarbons such as methane, unsaturated hydrocarbons such as ethylene or propylene, or aromatic hydrocarbons such as benzene, toluene or xylene.

In one embodiment, the fluid stream is a natural gas stream. In this embodiment, the partial hydrogen sulfide pressure in the fluid stream is typically at least 2.5 mbar. Particularly, a partial hydrogen sulfide pressure of at least 0.1 bar, especially at least 1 bar, and a partial carbon dioxide pressure of at least 0.2 bar, especially at least 1 bar, is present in the fluid stream. More preferably, there is a partial hydrogen sulfide pressure of at least 0.1 bar and a partial carbon dioxide pressure of at least 1 bar in the fluid stream. Even more preferably, there is a partial hydrogen sulfide pressure of at least 0.5 bar and a partial carbon dioxide pressure of at least 1 bar in the fluid stream. The partial pressures stated are based on the fluid stream on first contact with the absorbent in the absorption step. In preferred embodiments, a total pressure of at least 1.0 bar, more preferably at least 3.0 bar, even more preferably at least 5.0 bar and most preferably at least 20 bar is present in the fluid stream. In preferred embodiments, a total pressure of at most 180 bar, such as at most 90 bar, is present in the fluid stream. The total pressure is based on the fluid stream on first contact with the absorbent in the absorption step.

In some cases, for example in the case of removal of acid gases from natural gas for use as pipeline gas or sales gas, total absorption of carbon dioxide is undesirable. In one embodiment, the residual carbon dioxide content in the treated fluid stream is at least 0.5% by volume, preferably at least 1.0% by volume and more preferably at least 1.5% by volume.

In one embodiment, the absorbent is suitable for the selective removal of hydrogen sulfide from a fluid stream comprising hydrogen sulfide and carbon dioxide and allows high $H_2S$ clean-up selectively at low solvent circulation rates. Such an absorbent is useful in sulfur plant Tail Gas Treating Unit (TGTU) applications, in Acid-Gas Enrichment (AGE) processes to upgrade lean acid offgas from treating units to higher-quality Claus plant feed, or for the treatment of associated gases and refinery gases. In these processes, a total pressure in the range of 1.0 to 2.0 bar is usually present in the fluid stream. The total pressure is based on the fluid stream on first contact with the absorbent in the absorption step.

In TGTU applications, the partial hydrogen sulfide pressure in the fluid stream is typically at least 3 mbar. Particularly, a partial hydrogen sulfide pressure of at least 8 mbar, especially at least 10 mbar, and a partial carbon dioxide pressure of at least 30 mbar, especially at least 50 mbar, is present in the fluid stream.

In AGE applications, the partial hydrogen sulfide pressure in the fluid stream is typically at least 5 mbar. Particularly, a partial hydrogen sulfide pressure of at least 20 mbar, especially at least 50 mbar, and a partial carbon dioxide pressure of at least 500 mbar, especially at least 800 mbar, is present in the fluid stream.

Besides the removal of $H_2S$ and $CO_2$, further acid gases which may be present in the fluid stream, for example $SO_3$, $SO_2$, $CS_2$, HCN, COS and mercaptans, may also be removed. $SO_3$ and $SO_2$ tend to form heat stable salts with the amines, and may not be stripped off in the regeneration.

In the process of the invention, the fluid stream is contacted with the absorbent in an absorption step in an absorber, as a result of which carbon dioxide and hydrogen sulfide are at least partly scrubbed out. This yields a $CO_2$— and $H_2S$-depleted fluid stream and a $CO_2$— and $H_2S$-laden absorbent.

The absorber used is a scrubbing apparatus used in customary gas scrubbing processes. Suitable scrubbing apparatuses are, for example, random packings, columns having structured packings and having trays, membrane contactors, radial flow scrubbers, jet scrubbers, Venturi scrubbers and rotary spray scrubbers, preferably columns having structured packings, having random packings and having trays, more preferably columns having trays and having random packings. The fluid stream is preferably treated with the absorbent in a column in countercurrent. The fluid is generally fed into the lower region and the absorbent into the upper region of the column. Installed in tray columns are sieve trays, bubble-cap trays or valve trays, over which the liquid flows.

Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pall ring, Hiflow ring, Intalox saddle and the like. The random packings can be introduced into the column in an ordered manner, or else randomly (as a bed). Possible materials include glass, ceramic, metal and plastics. Structured packings are a further development of ordered random packings. They have a regular structure. As a result, it is possible in the case of packings to reduce pressure drops in the gas flow. There are various designs of structured packings, for example woven packings or sheet metal packings. Materials used may be metal, plastic, glass and ceramic.

The temperature of the absorbent in the absorption step is generally about 30 to 100° C., and when a column is used is, for example, 30 to 70° C. at the top of the column and 50 to 100° C. at the bottom of the column.

The process of the invention may comprise one or more, especially two, successive absorption steps. The absorption can be conducted in a plurality of successive component steps, in which case the crude gas comprising the acid gas constituents is contacted with a substream of the absorbent in each of the component steps. The absorbent with which the crude gas is contacted may already be partly laden with acid gases, meaning that it may, for example, be an absorbent which has been recycled from a downstream absorption step into the first absorption step, or be partly regenerated absorbent. With regard to the performance of the two-stage absorption, reference is made to publications EP 0 159 495, EP 0 190 434, EP 0 359 991 and WO 00100271.

The person skilled in the art can achieve a high level of hydrogen sulfide removal with a defined selectivity by, e.g., varying the conditions in the absorption step, such as the absorbent/fluid stream ratio, the column height of the absorber, the type of contact-promoting internals in the absorber, such as random packings, trays or structured packings, and/or the residual loading of the regenerated absorbent.

Since $CO_2$ is absorbed more slowly than $H_2S$, more $CO_2$ is absorbed in a longer residence time than in a shorter residence time. Therefore, longer residence times tend to decrease $H_2S$ selectivity. A higher column therefore brings about a less selective absorption. Trays or structured packings with relatively high liquid holdup likewise lead to a less selective absorption. The heating energy introduced in the regeneration can be used to adjust the residual loading of the regenerated absorbent. A lower residual loading of regenerated absorbent leads to improved absorption.

The process preferably comprises a regeneration step in which the $CO_2$— and $H_2S$-laden absorbent is regenerated. In the regeneration step, $CO_2$ and $H_2S$ and optionally further acid gas constituents are released from the $CO_2$— and $H_2S$-laden absorbent to obtain a regenerated absorbent. Preferably, the regenerated absorbent is subsequently recycled into the absorption step. In general, the regeneration step comprises at least one of the measures of heating, decompressing and stripping, for example with an inert fluid.

The regeneration step preferably comprises heating of the absorbent laden with the acid gas constituents, for example by means of a boiler, natural circulation evaporator, forced circulation evaporator or forced circulation flash evaporator. The absorbed acid gases are stripped out by means of the steam obtained by heating the solution. Rather than steam, it is also possible to use an inert fluid such as nitrogen. The term "inert fluid" is understood to relate to a fluid which does not undergo chemical reactions with acid gases, in particular carbon dioxide and hydrogen sulfide. The absolute pressure in the desorber is normally 0.1 to 3.5 bar, preferably 1.0 to 2.5 bar. The temperature is normally of 50° C. to 170° C., preferably 70° C. to 140° C., more preferred 110° C. to 135° C. The regeneration temperature depends on the regeneration pressure.

The regeneration step may alternatively or additionally comprise decompression. This includes at least one decompression of the laden absorbent from a high pressure as exists in the conduction of the absorption step to a lower pressure. The decompression can be accomplished, for example, by means of a throttle valve and/or a decompression turbine. Regeneration with a decompression stage is described, for example, in publications U.S. Pat. Nos. 4,537, 753 and 4,553,984.

The acid gas constituents can be released in the regeneration step, for example, in a decompression column, for example a flash vessel installed vertically or horizontally, or a countercurrent column with internals.

The regeneration column may likewise be a column having random packings, having structured packings or having trays. The regeneration column, at the bottom, has a heater, for example a forced circulation evaporator with circulation pump. At the top, the regeneration column has an outlet for the acid gases released. Entrained absorption medium vapors are condensed in a condenser and recirculated to the column.

It is possible to connect a plurality of decompression columns in series, in which regeneration is effected at different pressures. For example, regeneration can be effected in a preliminary decompression column at a high pressure typically about 1.5 bar above the partial pressure of the acid gas constituents in the absorption step, and in a main decompression column at a low pressure, for example 1 to 2 bar absolute. Regeneration with two or more decompression stages is described in publications U.S. Pat. Nos. 4,537,753, 4,553,984, EP 0 159 495, EP 0 202 600, EP 0 190 434 and EP 0 121 109.

The invention is illustrated in detail by the appended drawing and the examples which follow.

FIG. 1 is a schematic diagram of a plant suitable for performing the process of the invention.

Figure 2:
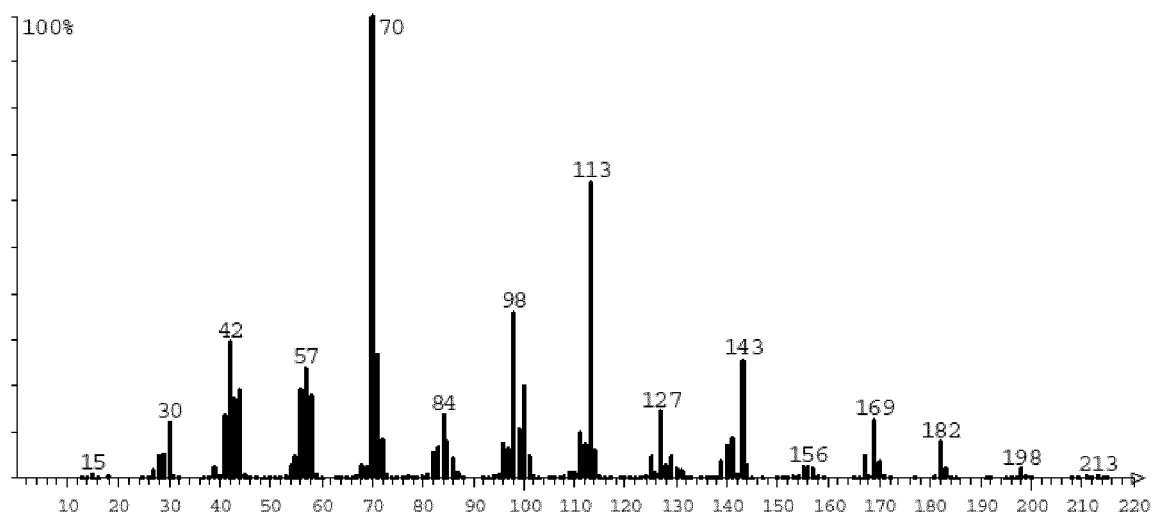
FIG. 2 shows the mass spectrum of 3-(4-methylpiperazin-1-yl)propyl-tert-butylamine (TBAP-MPIP).

FIG. 2 shows the mass spectrum of 3-(4-methylpiperazin-1-yl)propyl-tert-butylamine (TBAP-MPIP).

Figure 3:
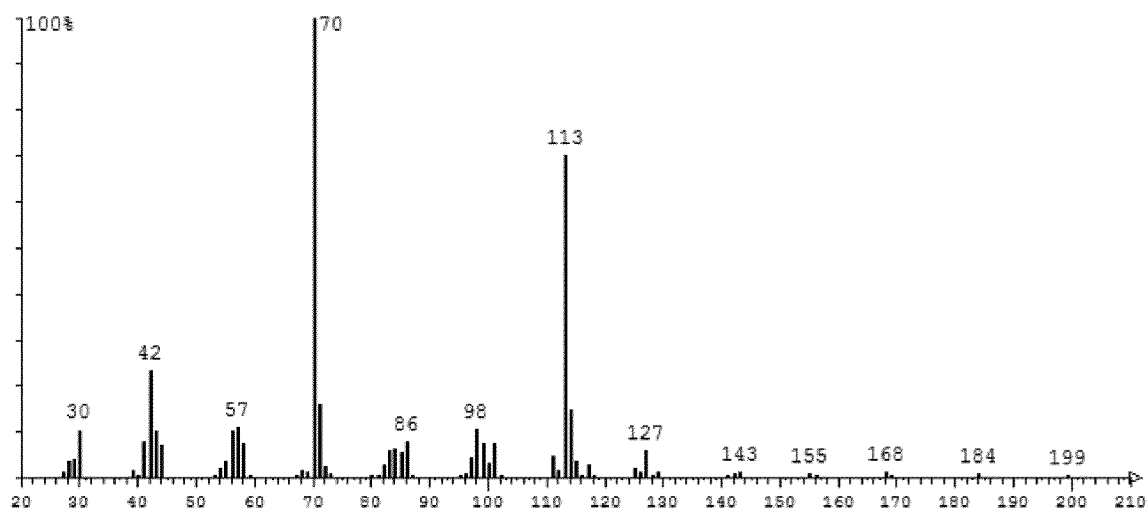
FIG. 3 shows the mass spectrum of 2-(4-methylpiperazin-1-yl)ethyl-tert-butylamine (TBAE-MPIP).

FIG. 3 shows the mass spectrum of 2-(4-methylpiperazin-1-yl)ethyl-tert-butylamine (TBAE-MPIP).

According to FIG. 1, a suitably pre-treated gas comprising hydrogen sulfide and carbon dioxide is fed into absorber A1 via inlet Z and contacted in countercurrent with regenerated absorbent which is fed into absorber A1 via absorbent line 1.01. The absorbent removes hydrogen sulfide and carbon dioxide from the gas by absorption, which affords a hydrogen sulfide- and carbon dioxide-depleted gas via offgas line 1.02.

Via absorbent line 1.03, heat exchanger 1.04, in which the $CO_2$— and $H_2S$-laden absorbent is heated up with heat from the regenerated absorbent conducted through the absorbent line 1.05, and absorbent line 1.06, the $CO_2$— and $H_2S$-laden absorbent is fed to desorption column D and regenerated.

Between absorber A1 and heat exchanger 1.04, one or more flash vessels may be provided (not shown in FIG. 1), in which the $CO_2$— and $H_2S$-laden absorbent is decompressed to, e.g., 3 to 15 bar.

From the lower part of desorption column D, the absorbent is conducted into boiler 1.07, where it is heated. The resulting steam is recycled into desorption column D, while the regenerated absorbent is fed back to absorber A1 via absorbent line 1.05, heat exchanger 1.04, in which the regenerated absorbent heats up the $CO_2$— and $H_2S$-laden absorbent and at the same time cools down itself, absorbent line 1.08, cooler 1.09 and absorbent line 1.01.

Instead of the depicted boiler, it is also possible to use other heat exchanger types for introducing energy, such as a natural circulation evaporator, forced circulation evaporator or forced circulation flash evaporator. In the case of these evaporator types, a mixed-phase stream of regenerated absorbent and steam is returned to the bottom of desorption column D, where the phase separation between the vapor and the absorbent takes place. The regenerated absorbent fed to heat exchanger 1.04 is either drawn off from the circulation stream conducted from the bottom of desorption column D to the evaporator, or conducted via a separate line directly from the bottom of the desorption column D to heat exchanger 1.04.

The $CO_2$— and $H_2S$-containing gas released in desorption column D leaves the desorption column D via offgas line 1.10. It is fed into a condenser with integrated phase separation 1.11, where it is separated from entrained absorbent vapor. In this and all the other plants suitable for performance of the process of the invention, condensation and phase separation may also be conducted separately from one another. Subsequently, the condensate is conducted through absorbent line 1.12 into the upper region of desorption column D, and a $CO_2$— and $H_2S$-containing gas is discharged via gas line 1.13.

The following abbreviations are used:
TBA: tert-butylamine
MDEA: methyldiethanolamine
TBAEE: 2-(2-tert-butylaminoethoxy)ethanol
M3ETB: (2-(2-(2-tert-butylaminoethoxy)ethoxy)ethyl) methyl ether TBAEPY: 1-[2-(tert-butylamino)ethyl]pyrrolidin-2-one
TBAP-MPIP: 3-(4-methylpiperazin-1-yl)propyl-tert-butylamine
TBAE-MPIP: 2-(4-methylpiperazin-1-yl)ethyl-tert-butylamine
DEAE-EPIP: 2-(4-ethylpiperazin-1-yl)ethyl-diethylamine

EXAMPLE 1: SYNTHESIS OF 3-(4-METHYLPIPERAZIN-1-YL)PROPYL-TERT-BUTYLAMINE (TBAP-MPIP)

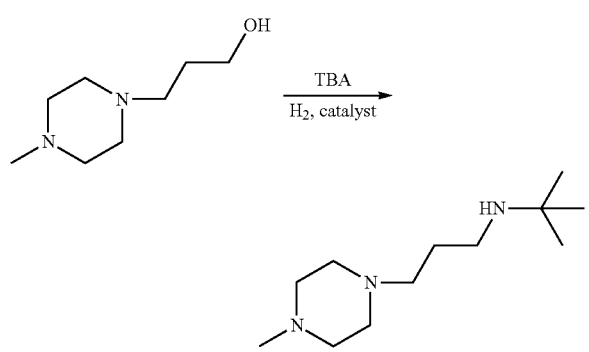

Synthesis of 3-(4-methylpiperazin-1-yl)propyl-tert-butylamine was carried out starting from 3-(4-methylpiperazin-1-yl)propan-1-ol using a high pressure autoclave with a volume of 2.5 L. The autoclave was equipped with a basket made from metal meshing for shaped catalyst bodies, a mechanical stirrer, baffles, an electrical heating mantle and an inlet for $H_2$ and $N_2$. 100 g of 3×3 mm pellets of a reduced-passivated catalyst containing Ni, Co, Cu, Sn on $Al_2O_3$ (obtained according to WO 2011/067199 A1, example 5) were filled into the basket, and a mixture of 730 g (10.0 mol) tert-butylamine and 200 g (1.264 mol) 3-(4-methylpiperazin-1-yl)propan-1-ol was introduced into the autoclave.

The autoclave was closed, and a test was performed to make sure the autoclave was sealed tightly at 200 bar by pressurizing with $N_2$. The autoclave was then purged three times with $N_2$ by pressurizing to 5 bar and releasing the pressure to 1 bar. Then, it was pressurized to 50 bar with hydrogen and under stirring, the contents were heated to 180° C. When this temperature was reached, the pressure was adjusted to 200 bar. After stirring for 15 hours under these conditions, the autoclave was allowed to cool down and depressurized. The liquid mixture was taken out and filtered.

The crude reaction product was analyzed by GC. The product was identified by GC-MS (molecule mass peak at 213 u) using electronic ionization and ionic ionization (GC-method: the column used was of type RTX5 Amin, length 30 m; diameter 0.32 mm; layer thickness 1.5 μm; temperature program: injection at 60° C., then directly temperature gradient 4° C./min until 280° C., then 35 min at 280° C.)

The crude product mixture contained 7.4% starting material, 43.0% product, 16.7% 1,3-bis(4-methyl-piperazin-1-yl)propane (GC area-%). Light boilers were removed at 80° C. and 20 mbar in a rotary evaporator, then the remaining crude product was distilled over a column filled with rings with a length of 30 cm, and one fraction (13.8 g) with a purity of 95% was retained while the rest (133.5 g) was redistilled over a smaller column with a length of 20 cm, yielding 48.6 g of product with a purity of 87%. The balance was mostly starting material which was considered not relevant for the desired testing.

The product was analyzed by GC-MS, and the mass spectrum was recorded using electronic ionization (EI) (conditions: mass range: 25-785 amu; ionization energy: 70 eV). Selected peaks are listed as follows with the exact mass divided by charge and the intensity relative to the most intense signal in parentheses. Additionally, molecular fragments are assigned to the peaks where possible.

m/z=213 (<1%, $M^+$); 198 (2%, $M^+$-$CH_3$); 183 (2%, $M^+$-2 $CH_3$); 182 (8%, $M^+$-$CH_3$—H); 169 (12%); 143 (25%, $M^+$-$NC_4H_9$); 127 (14%); 113 (63%, $C_6H_{13}N_2^+$, fragment N,N'-dimethylpiperazinyl$^+$), 101 (5%, N-methylpiperazine+H$^+$); 100 (20%, N-methyl-piperazine$^+$); 99 (10%); 98 (35%); 97 (6%); 96 (7%); 72 (8%) 71 (27%); 70 (100%), 69 (2%); 58 (18%, $C_4H_9^+$); 57 (24%); 56 (19%); 55 (5%); 54 (3%).

The expected molar peak $M^+$ was found. The structure was confirmed by analysis of the fragmentation pattern. The mass spectrum of TBAP-MPIP is shown in FIG. 2.

EXAMPLE 2: SYNTHESIS OF 2-(4-METHYLPIPERAZIN-1-YL)ETHYL-TERT-BUTYLAMINE (TBAE-MPIP)

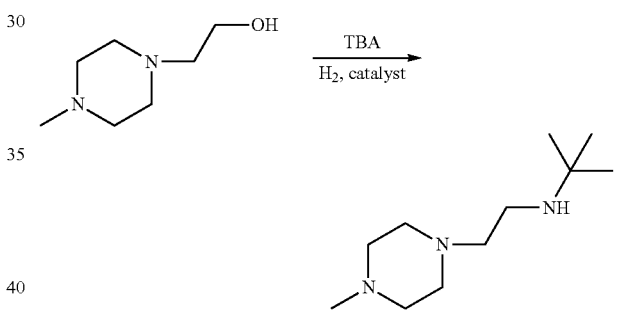

Using the same setup and equipment as in example 1, 200 g (1.387 mol) 1-(hydroxyethyl)-4-methylpiperazine were reacted with 1014 g (13.87 mol) tert-butylamine over 100 g of the catalyst described in example 1 at 120 bar and 180° C. After 8 h the reactor was allowed to cool to room temperature, depressurized, and a sample taken that was analyzed as described before. This showed a conversion of only 35% as calculated from the area-% of starting material and various products.

The crude reaction mixture was reacted for a further 12 h at 190° C. and 120 bar total pressure. A sample of the crude mixture as analyzed by gas chromatography showed a conversion of 90% and 66% product. Excess TBA and water were removed by evaporation under reduced pressure (60° C., 50 mbar) and the residue was purified by fractional distillation over a 15 cm column. At about 1 mbar the product distilled at 54° C. head temperature. A fraction of 90 g product with a purity of 93% was collected and used for further testing. The remainder was mostly starting material and not considered relevant for the evaluation.

The product was analyzed by GC-MS, and the mass spectrum was recorded using electronic ionization (EI) (conditions: mass range: 25-785 amu; ionization energy: 70 eV). Selected peaks are listed as follows with the exact mass divided by charge and the intensity relative to the most intense signal in parentheses. Additionally, molecular fragments are assigned to the peaks where possible.

m/z=199 (1%, M$^+$); 184 (1%, M$^+$-CH$_3$); 168 (1%, M$^+$—H, −2 CH$_3$); 114 (15%, C$_6$H$_{14}$N$_2$$^+$, N,N'-dimethylpiperazine$^+$); 113 (69%, C$_6$H$_{13}$N$_2$$^+$, fragment N,N'-dimethylpiperazinyl$^+$); 101 (5%, N-methylpiperazine+H$^+$); 100 (20%, N-methylpiperazine$^+$); 99 (10%); 98 (11%); 71 (16%); 70 (100%), 69 (1%); 58 (8%, C$_4$H$_9$$^+$); 57 (11%); 56 (10%); 55 (3%); 54 (2%).

The expected molar peak M$^+$ was found. The structure was confirmed by analysis of the fragmentation pattern. The mass spectrum of TBAE-MPIP is shown in FIG. 3.

EXAMPLE 3: RELATIVE VOLATILITY

The volatility of amines TBAP-MPIP and TBAE-MPIP in 30 wt.-% aqueous solutions was compared to that of amines M3ETB, MDEA and TBAEPY in 30% wt.-% aqueous solutions.

A glass condenser, which was operated at 5° C., was attached to a glass cylinder with a thermostated jacket. The glass cylinder was thermostated to 50° C., and 200 mL of the absorbent were introduced for each test. Over an experimental duration of 8 h, 30 L (STP)/h of N$_2$ were passed through the absorbent at ambient pressure. For each amine, the test was conducted three times. The condensate was analyzed by means of GC and Karl Fischer titration. The results are shown in the following table.

| Amine | Condensate [ml] | Water [wt %] | Amine [wt %] |
| --- | --- | --- | --- |
| M3ETB* | 30.1 | 99.2 | 0.7 |
| MDEA* | 27.1 | 99.4 | 0.7 |
| TBAEPY* | 28.8 | 99.5 | 0.2 |
| TBAP-MPIP | 30.3 | 99.7 | 0.3 |
| TBAE-MPIP | 29.28 | 99.3 | 0.7 |

*reference example

It is evident that TBAP-MPIP and TBAE-MPIP have a suitably low volatility.

EXAMPLE 4: ACID GAS LOADING CAPACITY

A loading experiment and subsequently a stripping experiment were conducted. A glass condenser, which was operated at 5° C., was attached to a glass cylinder with a thermostated jacket. Condensate obtained in the course of the experiment was returned to the glass cylinder so as to prevent distortion of the test results by partial evaporation of the absorbent.

The glass cylinder was initially charged with about 100 mL of unladen absorbent (30% by weight of amine in water). To determine the absorption capacity, at ambient pressure and 40° C., 8 L (STP)/h of CO$_2$ or H$_2$S were passed through the absorption liquid via a frit over a period of about 4 h. Subsequently, the loading of CO$_2$ or H$_2$S was determined as follows:

The determination of H$_2$S was effected by titration with silver nitrate solution. For this purpose, the sample to be analyzed was weighed into an aqueous solution together with about 2% by weight of sodium acetate and about 3% by weight of ammonia. Subsequently, the H$_2$S content was determined by a potentiometric turning point titration by means of silver nitrate. At the turning point, H$_2$S is fully bound as Ag$_2$S. The CO$_2$ content was determined as total inorganic carbon (TOC-V Series Shimadzu).

The laden solution was stripped by heating an identical apparatus setup to 80° C., introducing the laden absorbent and stripping it by means of an N$_2$ stream (8 L (STP)/h). After 60 min, a sample was taken and the CO$_2$ or H$_2$S loading of the absorbent was determined as described above.

The difference in the loading at the end of the loading experiment and the loading at the end of the stripping experiment gives the respective cyclic capacity.

The results are shown in the following table.

| Amine (30 wt.-% in water) | CO$_2$ loading [mol CO$_2$/mol$_{amine}$] after loading | CO$_2$ loading [mol CO$_2$/mol$_{amine}$] after stripping | Cyclic CO$_2$ capacity [mol CO$_2$/mol$_{amine}$] | H$_2$S loading [mol H$_2$S/mol$_{amine}$] after loading | H$_2$S loading [mol H$_2$S/mol$_{amine}$] after stripping | Cyclic H$_2$S capacity [mol H$_2$S/mol$_{amine}$] |
| --- | --- | --- | --- | --- | --- | --- |
| TBAEE* | 0.97 | 0.24 | 0.73 | n.d.** | n.d.** | n.d.** |
| MDEA* | 0.77 | 0.05 | 0.72 | 0.68 | 0.11 | 0.61 |
| TBAP-MPIP | 1.41 | 0.70 | 0.71 | 1.48 | 0.33 | 1.15 |
| TBAE-MPIP | 1.46 | 0.22 | 1.24 | 1.62 | 0.35 | 1.27 |
| DEAE-EPIP* | 1.48 | 0.13 | 1.35 | 0.98 | 0.31 | 0.67 |

*comparative example
**n.d. = not determined

It is evident that absorbents based on TBAP-MPIP and TBAE-MPIP have significantly higher acid gas loading capacities than absorbents based on TBAEE and MDEA at comparable or even higher cyclic acid gas capacities. DEAE-EPIP displays a similar cyclic CO$_2$ capacity as TBAE-MPIP, but the cyclic H$_2$S capacity of DEAE-EPIP is significantly lower than the capacity of both TBAP-MPIP and TBAE-MPIP.

EXAMPLE 5: pK$_A$ VALUE

The pKa values of the amino groups of MDEA, TBAP-MPIP, TBAE-MPIP and DEAE-EPIP were each determined by means of titration of an aqueous solution comprising 0.005 mol of amine per liter with hydrochloric acid (0.1 mol/L) at 20° C. The results are shown in the following table:

| # | Amine | pK$_A$ 1 | pK$_A$ 2 | pK$_A$ 3 |
| --- | --- | --- | --- | --- |
| 1* | MDEA | 8.7 | — | — |
| 2 | TBAP-MPIP | 10.74 | 7.68 | 5.80 |
| 3 | TBAE-MPIP | 10.01 | 8.82 | 5.47 |
| 4* | DEAE-EPIP | 10.32 | 8.61 | 6.2 |

*comparative example

It is evident that TBAP-MPIP and TBAE-MPIP have high first pK$_A$ values at relatively low temperatures, as prevail in the absorption step. A high pK$_A$ value at relatively low temperatures promotes efficient acid gas absorption. Additionally, the second $pK_A$ value is close to the pKa value of MDEA, which is in line with the higher $CO_2$ and $H_2S$ loading capacity per mole amine as measured in Example 4.

EXAMPLE 6: THERMAL STABILITY

The thermal stability of TBAP-MPIP (30 wt.-% in water) and TBAE-MPIP (25 wt.-% in water) was compared to both MDEA (40 wt.-% MDEA in water) and DEAE-EPIP (30 wt.-% DEAE-EPIP in water) with and without acid gas loading.

A cylinder (10 mL) was initially charged with the respective solution (8 mL) and the cylinder was closed. The cylinder was heated to 150° C. for 125 h. In the experiments conducted under acid gas loading, the acid gas loading of the solutions was 20 m³ (STP)/$t_{solvent}$ of $CO_2$ and 20 m³ (STP)/$t_{solvent}$ of $H_2S$. The decomposition level of the amines was calculated from the amine concentration measured by gas chromatography before and after the experiment. The results are shown in the following table.

| Aqueous Solution | Ratio of Degradation | |
|---|---|---|
| | Without Acid Gas Loading | With Acid Gas Loading |
| 40 wt.-% MDEA + 60 wt.-% $H_2O$* | 0.98 | 0.89 |
| 30 wt.-% TBAP-MPIP + 70 wt.-% $H_2O$ | 0.99 | 0.91 |
| 25 wt.-% TBAE-MPIP + 75 wt.-% $H_2O$ | 1.00 | 0.88 |
| 30 wt.-% DEAE-EPIP + 70 wt.-% $H_2O$* | 1.00 | 0.77 |

*comparative example

It is evident that TBAP-MPIP and TBAE-MPIP, respectively, have a stability in aqueous solutions comparable to MDEA, and higher than DEAE-EPIP.

The invention claimed is:

1. A process for removal of acid gases from fluid stream, wherein the fluid stream is brought into contact with an absorbent to obtain a treated fluid stream and a laden absorbent, the absorbent comprising a diluent and a compound of the general formula (I)

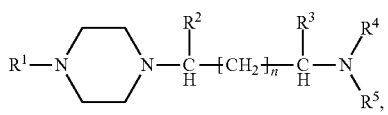

wherein
$R^1$ is $C_1$-$C_5$-alkyl;
$R^2$ is hydrogen;
$R^3$ is hydrogen;
$R^4$ is hydrogen or $C_1$-$C_5$-alkyl;
$R^5$ is isopropyl, tert-butyl or tert-pentyl;
and
n is 0 or 1,
wherein the absorbent comprises a total amount of 10% to 70% by weight of the compound of the general formula (I), based on the total weight of the absorbent.

2. The process according to claim 1, wherein the compound of the general formula (I) is selected from the group consisting of
3-(4-methylpiperazin-1-yl)propyl-tert-butylamine; and
2-(4-methylpiperazin-1-yl)ethyl-tert-butylamine.

3. The process according to claim 1, wherein the diluent is selected from the group consisting of water, organic solvents, and combinations thereof.

4. The process according to claim 1, wherein the absorbent comprises a tertiary amine or severely sterically hindered primary amine or severely sterically hindered secondary amine other than the compounds of the general formula (I), wherein severe steric hindrance is understood to mean a tertiary carbon atom directly adjacent to a primary or secondary nitrogen atom.

5. The process according to claim 1 for selective removal of hydrogen sulfide over carbon dioxide from a fluid stream.

6. The process according to claim 1, wherein the laden absorbent is regenerated by means of at least one of the measures of heating, decompressing and stripping.

7. An absorbent for the absorption of acid gases from a fluid stream, comprising a diluent and a compound of the general formula (I)

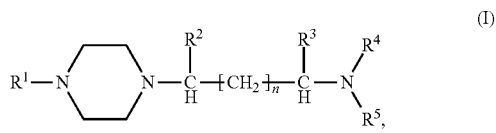

wherein
$R^1$ is $C_1$-$C_5$-alkyl;
$R^2$ is hydrogen;
$R^3$ is hydrogen;
$R^4$ is hydrogen or $C_1$-$C_5$-alkyl;
$R^5$ is isopropyl, tert-butyl or tert-pentyl;
and
n is 0 or 1,
wherein the absorbent comprises a total amount of 10% to 70% by weight of the compound of the general formula (I), based on the total weight of the absorbent.

8. The absorbent according to claim 7, wherein the compound of the general formula (I) is selected from the group consisting of
3-(4-methylpiperazin-1-yl)propyl-tert-butylamine; and
2-(4-methylpiperazin-1-yl)ethyl-tert-butylamine.

9. The absorbent according to claim 7, wherein the diluent is selected from the group consisting of water, organic solvents, and combinations thereof.

* * * * *